I'S011672967B2

(12) United States Patent
Gish et al.

(10) Patent No.: US 11,672,967 B2
(45) Date of Patent: Jun. 13, 2023

(54) SELF-CLEANING NEEDLELESS CONNECTOR

(71) Applicant: Grove Group, LLC, Calhoun, KY (US)

(72) Inventors: Nathan Gish, Calhoun, KY (US); Ross Hudson, Calhoun, KY (US); Josh Luttrell, Gallatin, TN (US)

(73) Assignee: GROVE GROUP, LLC, Calhoun, KY (US)

( * ) Notice: Subject to any disclaimer, the term of this patent is extended or adjusted under 35 U.S.C. 154(b) by 902 days.

(21) Appl. No.: 16/439,127

(22) Filed: Jun. 12, 2019

(65) Prior Publication Data
US 2019/0381306 A1    Dec. 19, 2019

Related U.S. Application Data

(60) Provisional application No. 62/684,405, filed on Jun. 13, 2018.

(51) Int. Cl.
| | | |
|---|---|---|
| *A61M 39/16* | (2006.01) | |
| *A61L 2/18* | (2006.01) | |
| *A61M 39/18* | (2006.01) | |
| *A61M 39/00* | (2006.01) | |

(Continued)

(52) U.S. Cl.
CPC ............ *A61M 39/162* (2013.01); *A61L 2/18* (2013.01); *A61M 39/165* (2013.01); *A61M 39/18* (2013.01); *A61L 2202/24* (2013.01); *A61M 5/001* (2013.01); *A61M 2039/009* (2013.01);

(Continued)

(58) Field of Classification Search
CPC ...... A61L 2/18; A61L 2202/24; A61M 5/001; A61M 39/16; A61M 39/162; A61M 39/165; A61M 39/18; A61M 2039/1066; A61M 2039/009; A61M 2039/1072
See application file for complete search history.

(56) References Cited

U.S. PATENT DOCUMENTS

| | | |
|---|---|---|
| 7,794,675 B2 | 9/2010 | Lynn |
| 7,857,793 B2 | 12/2010 | Raulerson et al. |
| 8,069,523 B2 | 12/2011 | Vaillancourt et al. |

(Continued)

FOREIGN PATENT DOCUMENTS

| | | |
|---|---|---|
| CA | 3100550 A1 | 12/2019 |
| EP | 3806927 A1 | 4/2021 |
| GB | 2059268 A | 4/1981 |

OTHER PUBLICATIONS

International Search Report and Written Opinion issued in Application No. PCT/US2019/036739 dated Jun. 12, 2019.

*Primary Examiner* — Mikhail Kornakov
*Assistant Examiner* — Richard Z. Zhang
(74) *Attorney, Agent, or Firm* — Gray Ice Higdon

(57) ABSTRACT

A self-cleaning needleless connector may include a connector body defining a fluid passageway including an inlet and an outlet, a cover disposed over at least the inlet of the connector body, an access point disposed at an inlet end of the cover, where in a first position the inlet is within the cover and in an second position the inlet is extended beyond the cover and configured to receive a male luer, a reservoir containing a cleaning agent, and an abrasive surface located in the cover that is in fluid communication with the cleaning agent, where the abrasive surface and the cleaning agent are configured to contact an exterior surface of the inlet to create friction.

20 Claims, 9 Drawing Sheets

(51) Int. Cl.
*A61M 5/00* (2006.01)
*A61M 39/10* (2006.01)

(52) U.S. Cl.
CPC ............... *A61M 2039/1066* (2013.01); *A61M 2039/1072* (2013.01)

(56) References Cited

U.S. PATENT DOCUMENTS

| | | |
|---|---|---|
| 8,137,303 B2 | 3/2012 | Stout et al. |
| 8,177,761 B2 | 5/2012 | Howlett et al. |
| 8,206,514 B2 | 6/2012 | Rogers et al. |
| 8,480,968 B2 | 7/2013 | Lynn |
| 8,628,501 B2 | 1/2014 | Hadden |
| 9,192,449 B2 | 11/2015 | Kerr et al. |
| 9,782,507 B2 | 10/2017 | Ma et al. |
| 9,844,258 B2 | 12/2017 | Trebella et al. |
| 2007/0112333 A1 | 5/2007 | Hoang et al. |
| 2008/0132880 A1* | 6/2008 | Buchman ............. A61M 25/00 604/533 |
| 2008/0147047 A1 | 6/2008 | Davis et al. |
| 2008/0235888 A1 | 10/2008 | Vaillancourt et al. |
| 2009/0028750 A1 | 1/2009 | Ryan |
| 2009/0041619 A1 | 2/2009 | Cady et al. |
| 2009/0137969 A1 | 5/2009 | Colantonio et al. |
| 2010/0100056 A1* | 4/2010 | Cawthon ............. A61M 39/165 604/256 |
| 2010/0200017 A1* | 8/2010 | Kerr ..................... A61L 2/235 15/104.93 |
| 2010/0296968 A1 | 11/2010 | Cady |
| 2011/0054440 A1 | 3/2011 | Lewis et al. |
| 2011/0064512 A1 | 3/2011 | Shaw et al. |
| 2011/0295235 A1 | 12/2011 | Fangrow |
| 2012/0078203 A1 | 3/2012 | Gaube et al. |
| 2014/0155868 A1 | 6/2014 | Nelson et al. |
| 2014/0228773 A1 | 8/2014 | Burkholz |
| 2015/0000061 A1 | 1/2015 | Rogers et al. |
| 2015/0217104 A1 | 8/2015 | Biehl et al. |
| 2015/0273199 A1 | 10/2015 | Adams et al. |
| 2016/0000062 A1 | 1/2016 | Chen et al. |
| 2016/0015931 A1 | 1/2016 | Ryan et al. |
| 2016/0106968 A1 | 4/2016 | Solomon et al. |
| 2016/0271312 A1 | 9/2016 | Lance et al. |
| 2017/0050012 A1 | 2/2017 | Alpert |
| 2017/0157386 A1 | 2/2017 | Ferlic |
| 2017/0120028 A1 | 5/2017 | Burkholz et al. |
| 2017/0203087 A1 | 7/2017 | Ryan et al. |
| 2017/0274198 A1 | 9/2017 | Dupont et al. |
| 2017/0333156 A1 | 11/2017 | Ready et al. |

\* cited by examiner

SELF-CLEANING NEEDLELESS CONNECTOR

BACKGROUND

Needleless connectors connect to the end of a vascular catheter, urinary catheter, IO catheter, or the like and function as an access point for infusion, aspiration, etc. Accordingly, needleless connectors also function as a gate keeper for microbial intrusion into the vascular catheter and ultimately the bloodstream of a patient. The disinfection process for a needleless connector is a critical determiner of whether there is microbial intrusion, and the quantity thereof, into the vascular catheter, urinary catheter, or IO catheter.

Conventional needleless connectors require an active disinfection process by a clinician, for example through wiping the connection point with a disinfecting wipe for a predetermined length of time (e.g. about 30 seconds). This process is prone to human error, as clinicians may not properly disinfect the entire surface of the needleless connector. For example, a clinician may not disinfect the surface long enough or may forget to disinfect the surface at all. There exists a need in the art for a needleless connector that automatically disinfects the connection surface, minimizing the risk of human error, and ultimately for minimizing the risk of infection or death to the patient, the mortality rate for such infections ranging from 12%-25%.

SUMMARY

The herein-described embodiments address these and other problems associated with the art in a first aspect by a self-cleaning needleless connector, including: a connector body that defines a fluid passageway with an inlet and an outlet; a cover disposed over at least the inlet of the connector body; an access point located at the end of the inlet of the cover and the access point is movable between a first position and an second position, where when in the first position the inlet is within the cover and when in the second position the inlet is extended beyond the cover and configured to receive a male luer; a reservoir containing a cleaning agent; and an abrasive surface located in the cover and in fluid communication with the cleaning agent, where the abrasive surface is configured to contact an exterior surface of the inlet.

In some embodiments, the cover is movable between an extended position and a retracted position. In some such embodiments, a spring mechanically biases the cover to the extended position and the access point is movable to the second position upon user-actuated compression of the spring. In other such embodiments, a piston moves laterally towards the outlet end of the connector as the cover moves from the extended position to the retracted position to accommodate fluidic movement of the cleaning agent.

In some embodiments, the cleaning agent is 70% isopropyl alcohol. In some embodiments, the abrasive surface is a plurality of bristles.

In some embodiments, the cover is rotatable about an axis of rotation that is generally aligned with the connector body. In some such embodiments, the cover is rotated about the axis of rotation simultaneous with the cover being moved to a retracted position by user-actuated compression of a spring, where the spring mechanically biases the cover to an extended position.

In some embodiments, the access point includes a first portion and a second portion, where the first and the second portion are configured to retract into the cover when the access point moves from the first position to the second position. In other embodiments, the cover further includes one or more sealants to minimize leakage of the cleaning agent. In still other embodiments, the exterior surface of the inlet includes a plurality of threads and the abrasive surface is configured to contact the plurality of threads as the cover moves from the extended position to the retracted position.

In another aspect, a self-cleaning needleless connector includes: a connector body defining a fluid passageway with an inlet and an outlet, where the inlet additionally includes a plurality of threads and is configured to receive a male luer; a cover located over at least the inlet of the connector body, where the cover is movable between an extended position and a retracted position, where when in the extended position the inlet is within the cover and in the retracted position the inlet is extended beyond the cover; a septum located proximate an inlet end of the cover; a reservoir containing a cleaning agent, where the reservoir fluidly connects the connector body and the cover; and an abrasive surface located inside of the cover and in fluid communication with the cleaning agent, where the abrasive surface is configured to contact the threads (to create friction) as the access point moves from the closed position to the open position.

In some embodiments, the cover is rotatable about an axis of rotation that is generally aligned with the connector body. In some such embodiments, the cover is rotated about the axis of rotation simultaneous with the cover being moved to the retracted position by user-actuated compression of a spring, where the spring mechanically biases the cover to the extended position.

In some embodiments, the septum is a split septum and is recessed into the inlet end of the cover. In other embodiments, the abrasive surface is a plurality of bristles.

In yet another aspect, a method of cleaning an inlet of a needless connector, where the needleless connector includes a connector body defining a fluid passageway including an inlet and an outlet, a cover located over at least the inlet, and an access point disposed at an inlet end of the cover, the access point being movable between a closed position and an open position, the method including: transferring a cleaning agent from a reservoir to an abrasive surface; directly contacting the abrasive surface with the cleaning agent; and moving the access point from the closed position, where the inlet is within the cover to the open position where the inlet is extended beyond the cover and configured to receive a male luer.

In some embodiments, a spring mechanically biases the access point to the closed position and moving the access point from the closed position further includes compressing, by a user, the spring. In other embodiments, the method may additionally include rotating the cover about an axis of rotation that is generally aligned with the connector body, generating friction between the abrasive surface and the inlet contact. In some such embodiments, the rotating of the cover is simultaneous with moving the access point from the closed portion to the open position.

The term "needleless connector" as used herein refers to a device with multiple connection points, including for example, one side that may connect the surface of the needleless connector to IV-tubing or the like, and a second side that may be a male luer end or the like. These types of apparatuses may also be referred to as "end caps," "injection caps," "luer-activated devices," "injection ports," or "mechanical valves." However, as used herein, the term "needleless connector" encompasses all of these aforementioned apparatuses and includes all the various types and designs in this category of products.

These and other advantages and features, which characterize the invention, are set forth in the claims annexed hereto and forming a further part hereof. However, for a better understanding of the invention, and of the advantages and objectives attained through its use, reference should be made to the Drawings, and to the accompanying descriptive matter, in which there is described example embodiments of the invention. This summary is merely provided to introduce a selection of concepts that are further described below in the detailed description, and is not intended to identify key or essential features of the claimed subject matter, nor is it intended to be used as an aid in limiting the scope of the claimed subject matter.

BRIEF DESCRIPTION OF THE DRAWINGS

FIG. 1A is perspective view of the needleless connector in a closed (storage) position. FIG. 1B is a perspective view of the needleless connector of FIG. 1A in an open (use) position.

FIG. 2A is cross-sectional view of the needleless connector in a closed (storage) position. FIG. 2B is a cross-sectional view of the needleless connector in an open (use) position.

FIG. 4A is perspective view of the needleless connector in a closed (storage) position. FIG. 4B is a cross-sectional view of the self-cleaning needleless connector of FIG. 4A.

DETAILED DESCRIPTION

In some embodiments discussed hereinafter, a self-cleaning needleless connector may generally include a reservoir containing a cleaning agent and an abrasive surface disposed within the connector housing, where the abrasive surface may be in fluid communication with the cleaning agent. The abrasive surface may contact an exterior surface of the inlet as an access point moves from a closed position to an open position.

Figure 1A:
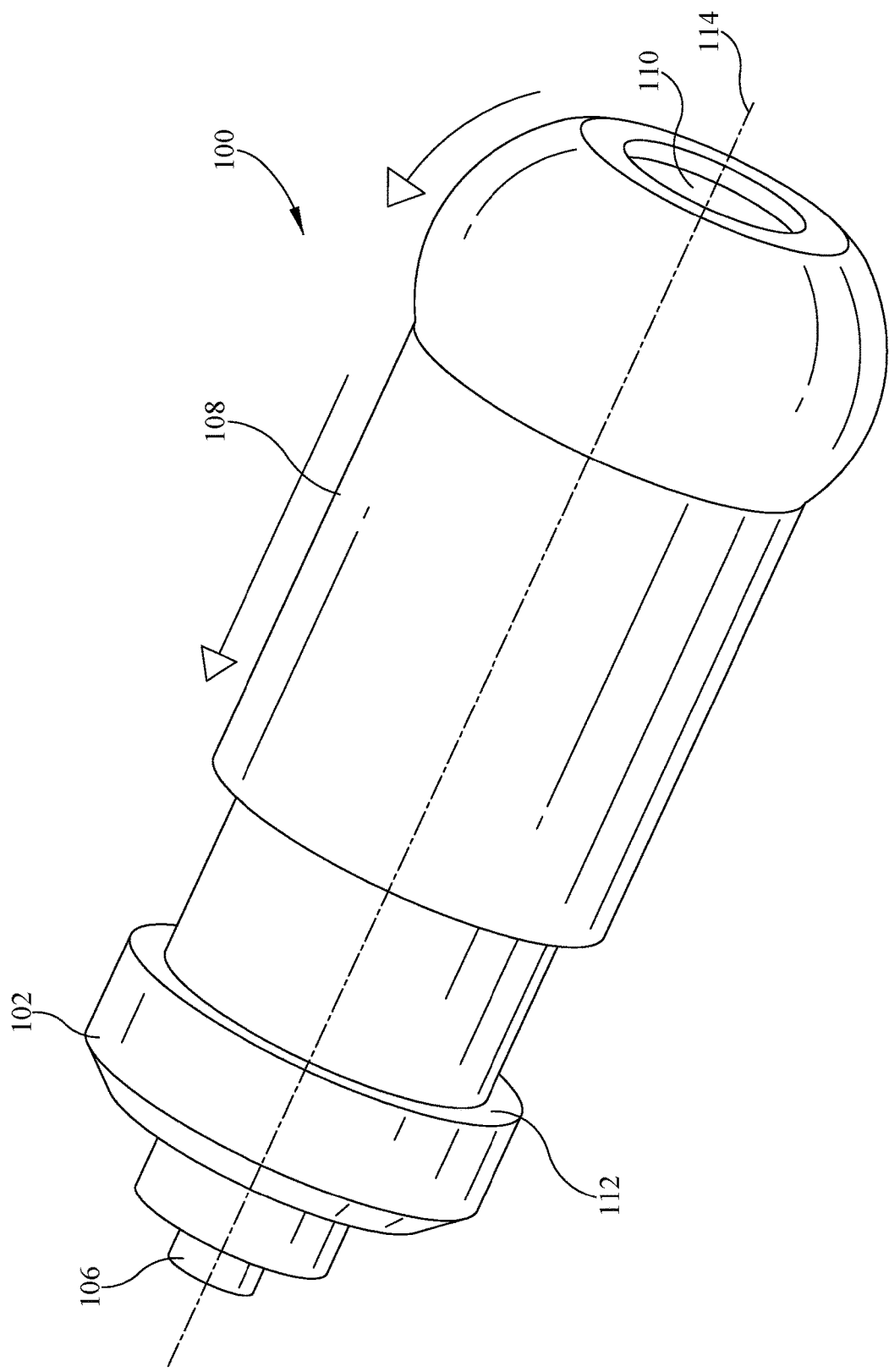
FIGS. 1A-B are perspective views of a self-cleaning needleless connector consistent with some embodiments of the invention.
Figure 1B:
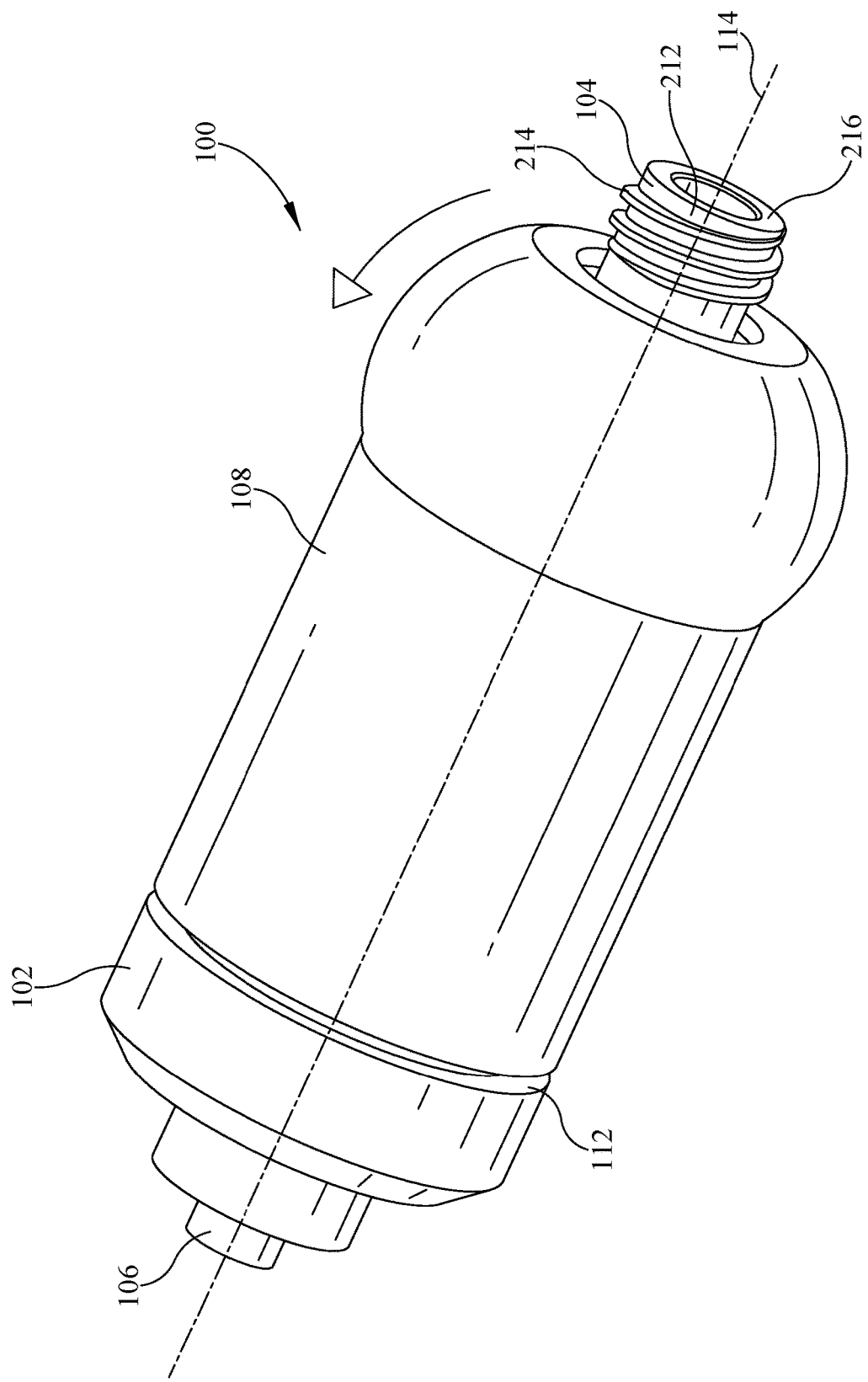

Turning now to the drawings, wherein like numbers denote like parts throughout the several views, FIGS. 1A-B illustrate an exemplary embodiment of a self-cleaning needleless connector 100 in storage position (FIG. 1A) and an use position (FIG. 1B). The self-cleaning needleless connector 100 may include a connector body 102 with an inlet 104 and an outlet 106, where the inlet 104 and the outlet 106 define a passageway (not visible in FIGS. 1A-B) through which fluid may flow. The fluid passageway of the needless connector described herein is not limited to a single type of fluid displacement; it is to be understood that in some instances the needleless connector may have positive, negative, or neutral fluid displacement.

Figure 3:
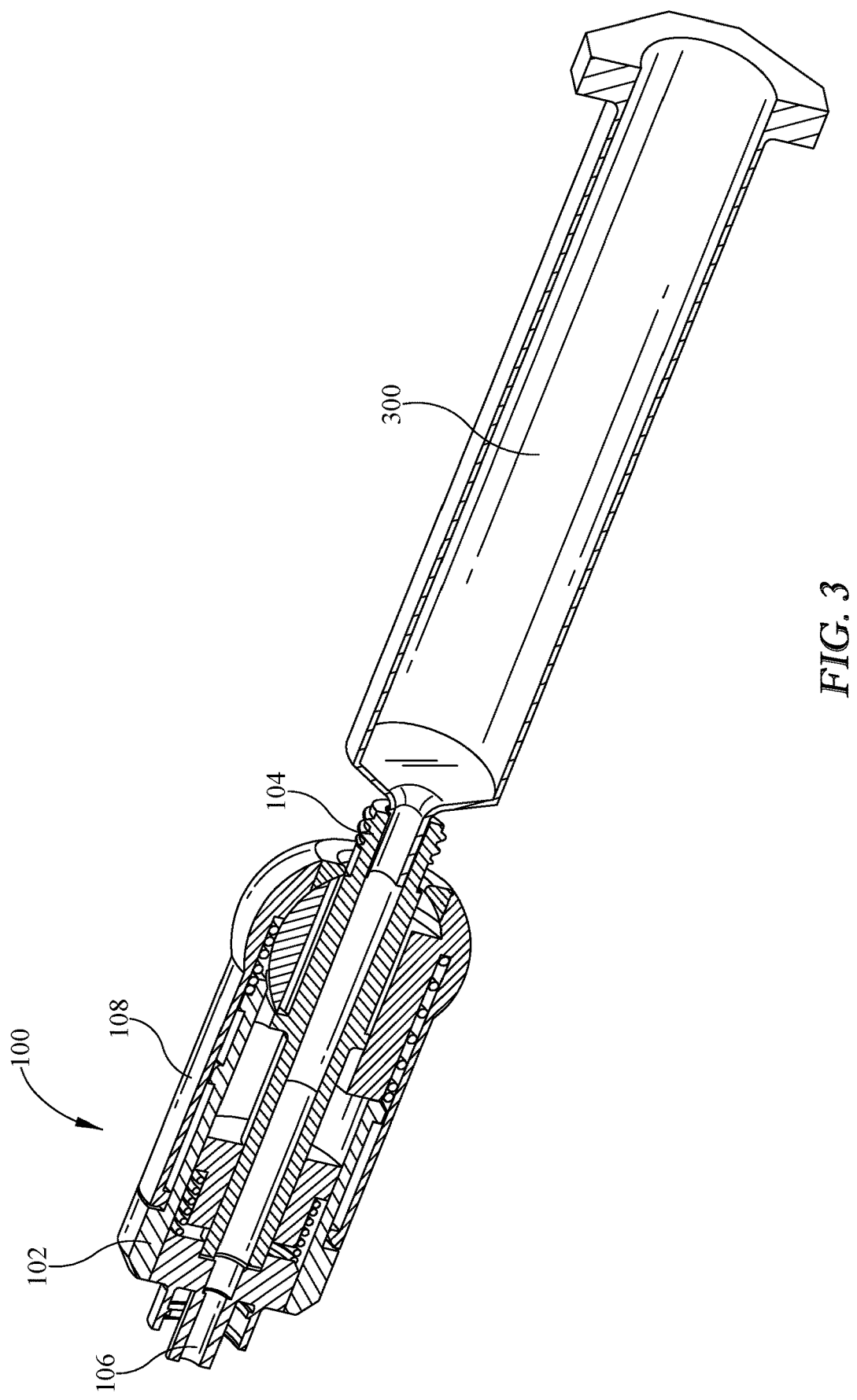
FIG. 3 is a perspective view of the self-cleaning needleless connector of FIG. 1A in an open position connected to an exemplary syringe consistent with some embodiments of the invention.

A sleeve or cover 108 may be positioned to envelop at least a portion of the connector body 102, including at least the inlet 104. In some instances, the cover 108 may only be disposed over the inlet 104 of the connector body; while in other instances, the cover 108 may be disposed over a substantial portion of the connector body 102 (as illustrated in FIGS. 1A-B). The cover 108 may additionally include an access point 110 that, as will be described in detail herein, moves from a first position to a second position (e.g. opens and closes) to expose the inlet 104 (see FIG. 1B), the inlet 104 being configured to receive a male luer (for example, of a syringe). For example, FIG. 3 illustrates a syringe 300 coupled with the inlet 104 of the needleless connector 100. As an example, when the access point 110 is in a closed position, the inlet 104 may be enclosed or protected within the cover 108, while when the access point 110 is in an open position, the inlet 104 may be exposed and extend out of the cover 108. In some instances, the access point 110 may be a solid surface that may be configured to retract (e.g. through rotation upward) into the cover 108 when the access point 110 moves from the first, closed position (FIG. 1A) to the second, open position (FIG. 1B). In other instances, the access point 110 may be in the form of a septum, such as a split septum 410, 510 illustrated in FIGS. 4A-B and 5.

As will also be described in detail herein, the cover 108 may also move from a first, expanded position, such as illustrated in FIG. 1A, to a second, retracted position, such as illustrated in FIG. 1B. For example, a user (such as a clinician) may actuate this lateral movement of the cover 108 in order to expose the inlet 104 of the connector body 102. In some instances, a lip or protrusion 112 may be positioned proximate the outlet 106 of the connector body 102 and may function as a stop for the cover 108 so as to prevent a user from retracting the cover 108 too far during retraction.

Figure 2A:
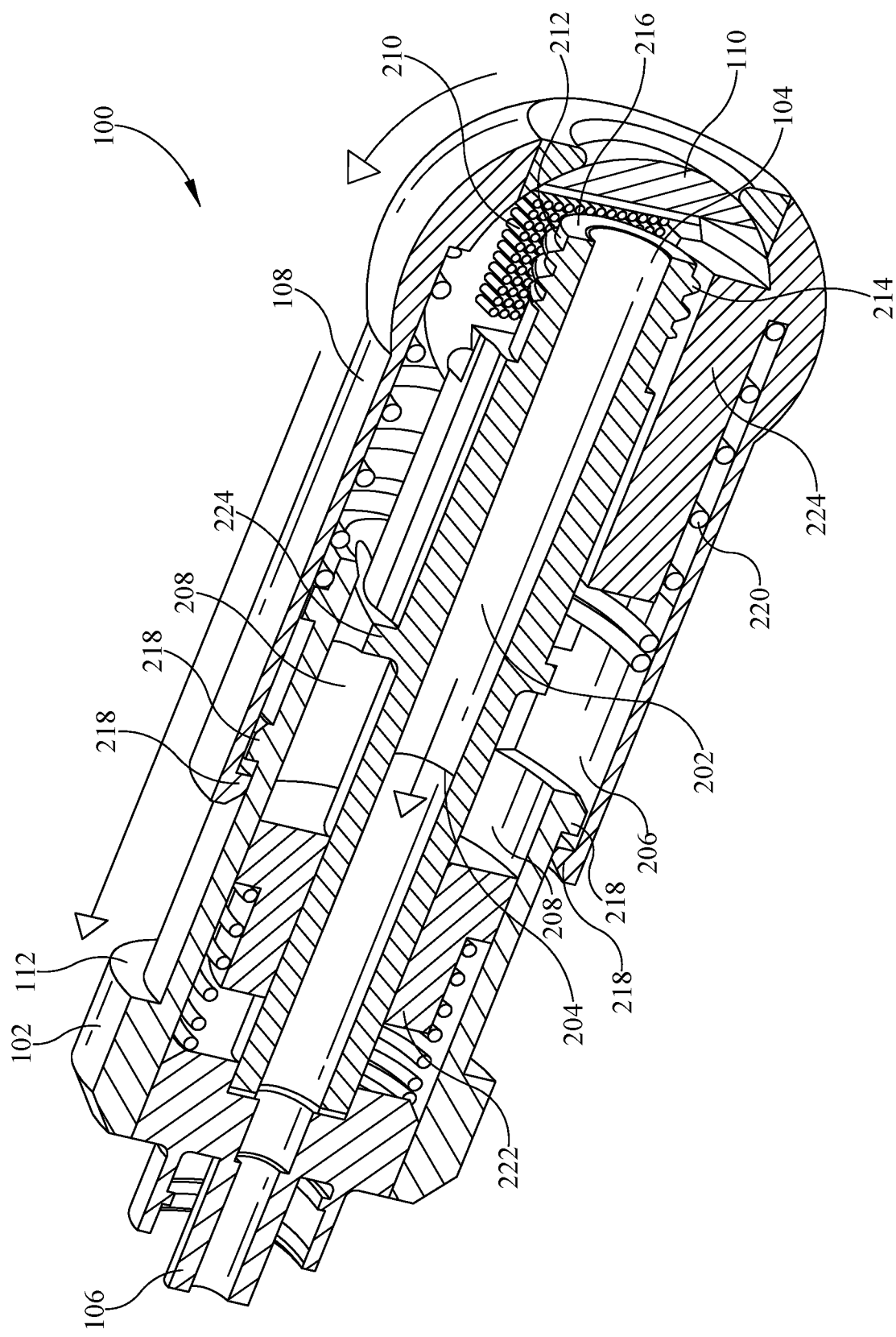
FIGS. 2A-B are cross-sectional views of the self-cleaning needleless connector of FIGS. 1A-B, respectively.

In some instances, there may be a spring 220 that mechanically biases the cover 108 to an extended position (FIG. 2A). This biasing may prevent inadvertent exposure of the inlet 104 of the connector body 102 to the environment. In such instances, a user may actuate the compression of the spring 220 by moving the cover 108 laterally towards the outlet 106 of the connector body 102 along an axis 114 running along the connector body 102 between the inlet 104 and the outlet 106. The user-actuated compression of the spring 220 results in the retraction of the cover 108, the movement of the access point 110 from a first position (closed) to a second position (open), and the exposure of the inlet 104 to the external environment. In some instances, the cover 108 may also rotate around the connector body 102. As an example, a user may rotate the cover 108 around the axis 114 of rotation running along the connector body 102 between the inlet 104 and the outlet 106 prior to, or simultaneous with, compressing the spring 220 to expose the inlet 104.

Figure 2B:
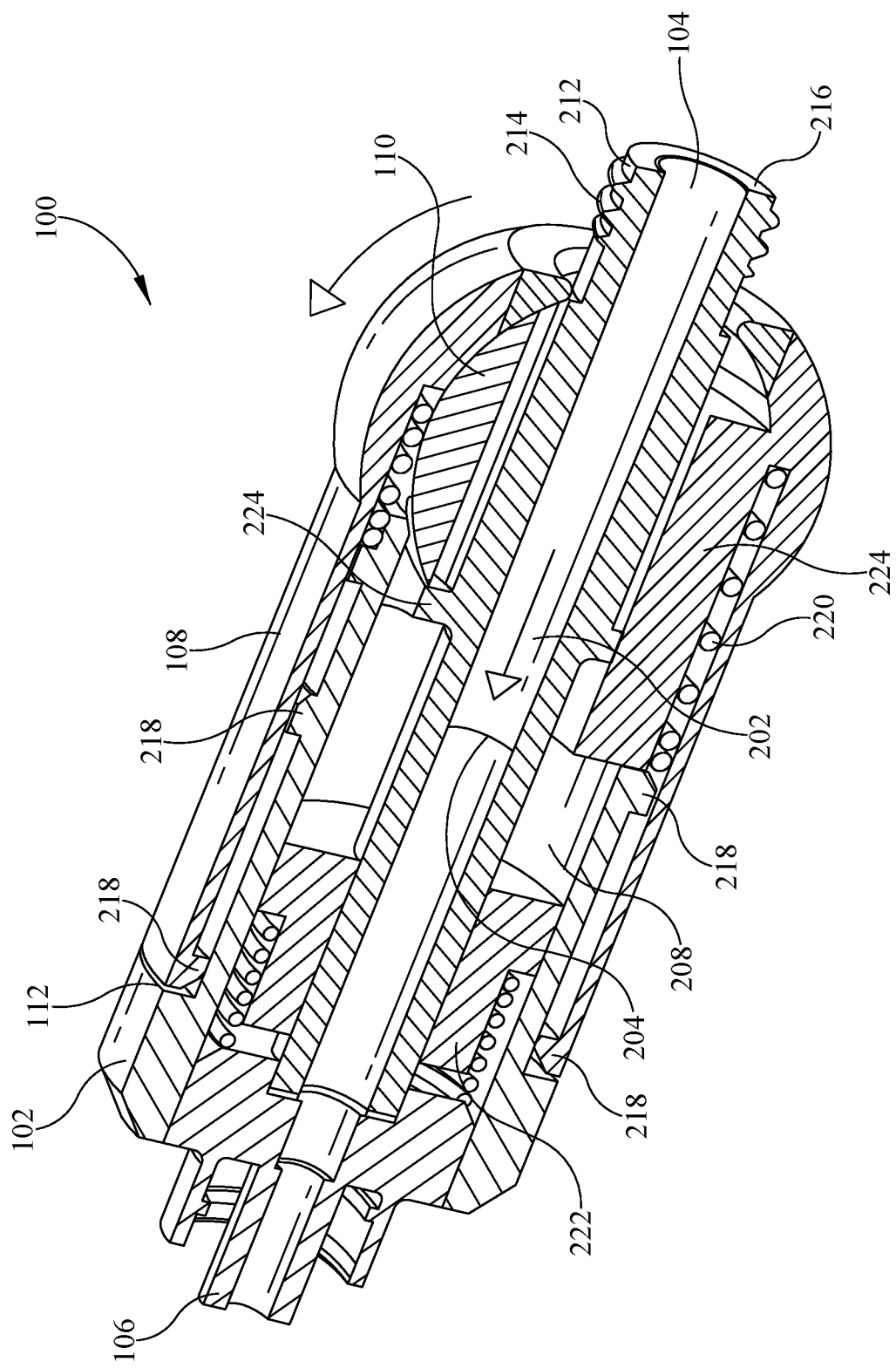

Referring now to FIGS. 2A-B, which illustrate cross-sectional views depicting the internal components of the self-cleaning needleless connector 100 in both a storage position (FIG. 2A) and a use position (FIG. 2B). As described previously, the self-cleaning needleless connector 100 may include a connector body 102 with an inlet 104 and an outlet 106, where the inlet 104 and the 106 define a passageway 202 through which fluid may flow, as indicated by the arrow in FIGS. 2A-B. In some instances, the fluid passageway 202 may include a mechanical valve 204, such as a check valve, in order to control the flow of the fluid through the passageway 202, and in some instances to prevent backflow.

In addition to the fluid passageway 202, the interior of the connector body 102 and the cover 108 collectively form a plurality of internal voids 206. At least of portion of these internal voids 206 form a reservoir 208 for containing a liquid cleaning agent. It is to be understood that the specific placement of the reservoir is not limiting, and that such a reservoir may be place in any location suitable to allow fluid communication with the abrasive surface 210 (described in detail herein). Such a cleaning agent may include, but not be limited to, may be 70% isopropyl alcohol, chlorhexidine gluconate mixed with 70% isopropyl alcohol (also known as "CHG+alcohol"), and 10% povidone-iodinechlorhexidine, glutaraldehyde, etc. Generally, a cleaning agent may be any suitable biocidal substance capable of disinfecting a surface.

When the self-cleaning needleless connector 100 is in a storage position, such as illustrated in FIG. 2A, the reservoir 208 and cleaning agent contained therein may be fluidly coupled with an abrasive surface 210 located within the cover 108. The abrasive surface 210, in fluid communication with the cleaning agent, may be configured to physically contact an exterior surface 212 of the inlet 104 such that the cleaning agent is also in contact with the exterior surface 212 of the inlet 104. In some instances, the exterior surface 212 of the inlet 104 may additionally include one or more threads 214 to facilitate the receipt of the male luer, and as such, it may also in some instances, be desirable for the abrasive surface 210 to be able to contact the surface area in between the threads 214. In some instances, the abrasive surface 210 may include a plurality of bristles (as illustrated in FIG. 2A), these bristles may be constructed of rubber, silicone, nylon, nylon-polyester, polyester, natural fibers, or any other suitable material. In such instances, the cleaning agent may flow between the bristles of the abrasive substance 210 and contact the exterior surface 212 of the inlet 104, including, where present, in-between the threads 214. Generally, the abrasive surface 210 may be any surface that is capable of generating friction when in contact with the exterior surface 212 of the inlet 104, so as to allow the cleaning agent to disinfect the exterior surface 212 of the inlet 104. Contact by the abrasive surface 210 and cleaning agent with the exterior surface 212 of the inlet 104 may be critical to the disinfection process. For example, the required contact time required for disinfecting a surface may vary by the cleaning agent, but may range from 15 seconds to as long ten (10) minutes. Use of a self-cleaning needleless connector, such as any of the embodiments described herein, may allow this contact time to occur without action of the clinician.

In some instances, the abrasive substance 210 may completely circumscribe the exterior surface 212 of the inlet 104. In other instances, there may be more than one abrasive surface 210. In such instances, the abrasive surfaces 210 may be placed on two opposing sides of the exterior surface 212 of the inlet 104 (as illustrated in FIG. 2A). In other such instances, the abrasive surfaces 212 may be placed on two opposing sides of the exterior surface 212 of the inlet 104 (as illustrated in FIG. 2A) and between the end 216 of the inlet 104 and the access point 110, so as to also contact and disinfect the end 216 of the inlet 104. It is to be understood that the specific placement of the abrasive surface(s) 210 is not to be construed as limiting; the abrasive surface(s) 210 may be located anywhere within the cover 208 that allows for contact with the exterior surface 212 of the inlet 104 when the cover 108 is an extended position (FIGS. 1A, 2A). The abrasive surface(s) 210 may also be in contact with and generate friction at the exterior surface 212 of the inlet 104 when the cover 108 is moved from an extended position to a retracted position (FIGS. 1B, 2B).

Additionally, in some instances, the self-cleaning needleless connector 100 may also include a piston 222 that moves laterally along the axis 114 running along the connector body 102 between the inlet 104 and the outlet 106 as the cover 108 moves from the extended position to the retracted position upon user actuation. The movement of this piston 222 may increase the volume of the portion of the reservoir 208 contained within the connector body 102, in order to accommodate the cleaning agent as it is forced laterally when the cover 108 retracted. The cover 108 may, in some instances, contain internal seals 224 that may eliminate or reduce the leakage of the cleaning agent from the cover 108 when in a retracted position.

As previously mentioned, in some instances, the cover 108 may rotate about an axis of rotation 114 generally aligned with the connector body 102. This rotation may also facilitate contact of the abrasive surface(s) 210, and fluidly coupled cleaning agent, with the exterior surface 212 of the inlet 104. In some instances, a clinician may rotate the self-cleaning needleless connector 100 prior to connector to a syringe or the like as an additional precautionary measure for disinfecting the inlet 104. In other instances, the rotation of the cover 108 may be simultaneous with the cover 108 being moved from the extended position (FIGS. 1A, 2A) to the retracted position (FIGS. 1B, 2B).

In some instances, the cover 108 and/or the connector body 102 may include one or more sealants 218 that may eliminate or reduce the leakage of the cleaning agent from the self-cleaning needleless connector 100 though the area where the cover 108 and the connector body 102 interface. In some instances, the sealant 218 may be a mechanical seal constructed of an acrylic resin, butyl rubber, epoxy, latex, polyurethane, rubber, silicone, urethane, and/or any other sealing material capable of providing a seal to eliminate or minimize leakage of the cleaning agent. Although illustrated in FIGS. 2A-B as a sealing protrusion incorporated as a part of the connector body 102 and the cover 108, the sealant 218 is not so limited. In other instances, the sealant 218 may be one or more O-rings/gasket disposed on the cover 108 and/or the connector body 102, or any other sealing structure known.

Figure 4A:
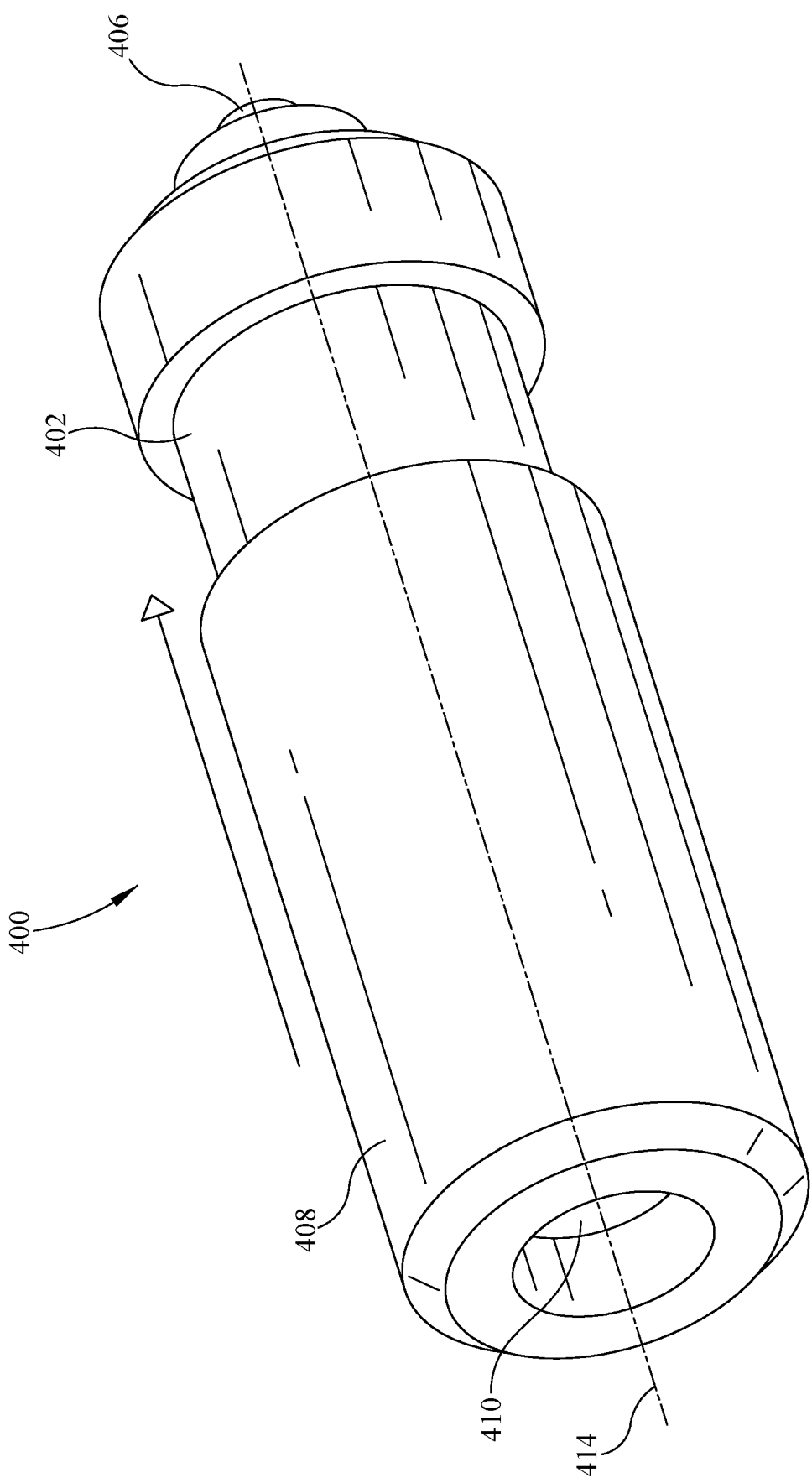
FIGS. 4A-B are views of a self-cleaning needleless connector consistent with some embodiments of the invention.
Figure 4B:
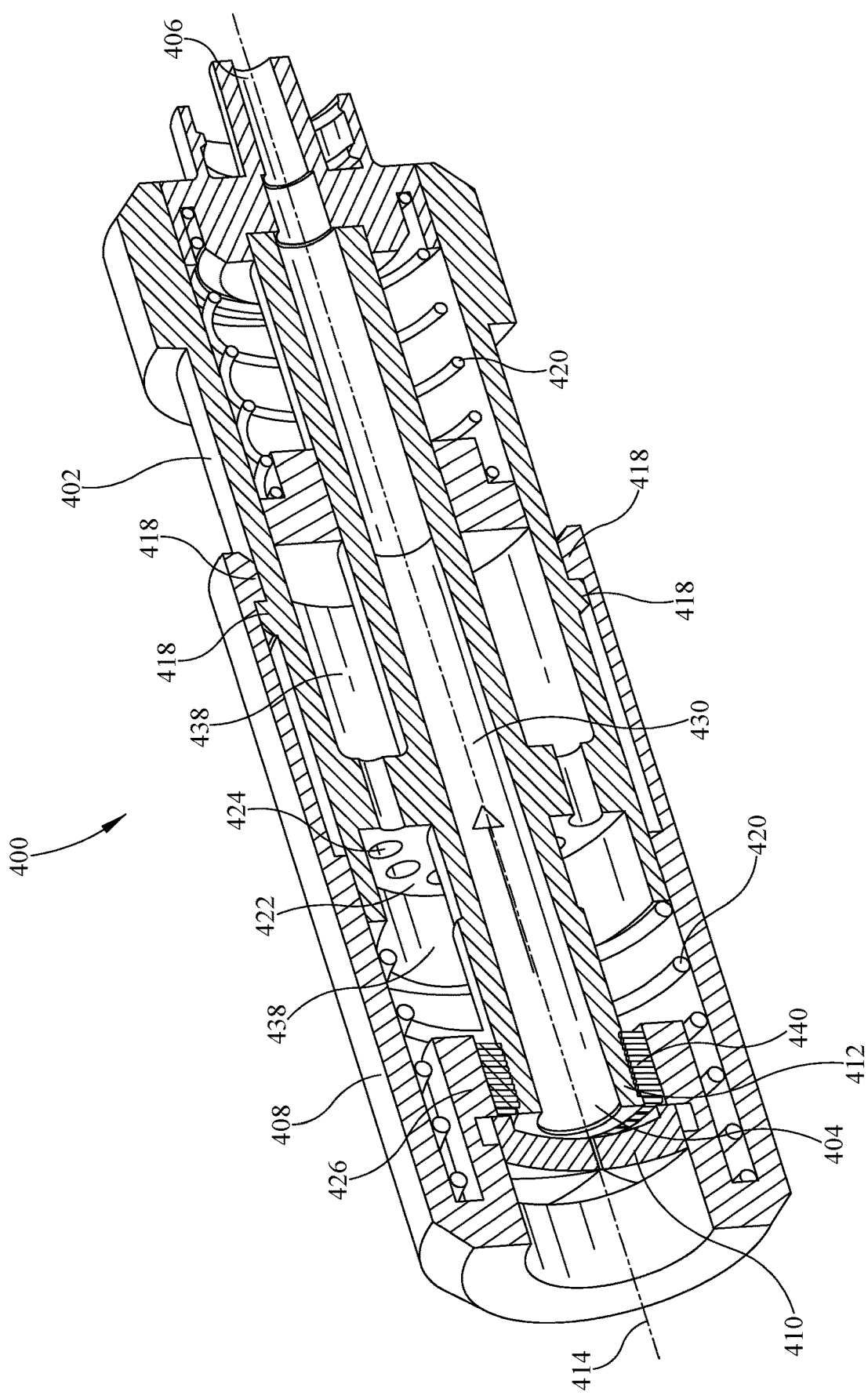
Figure 5:
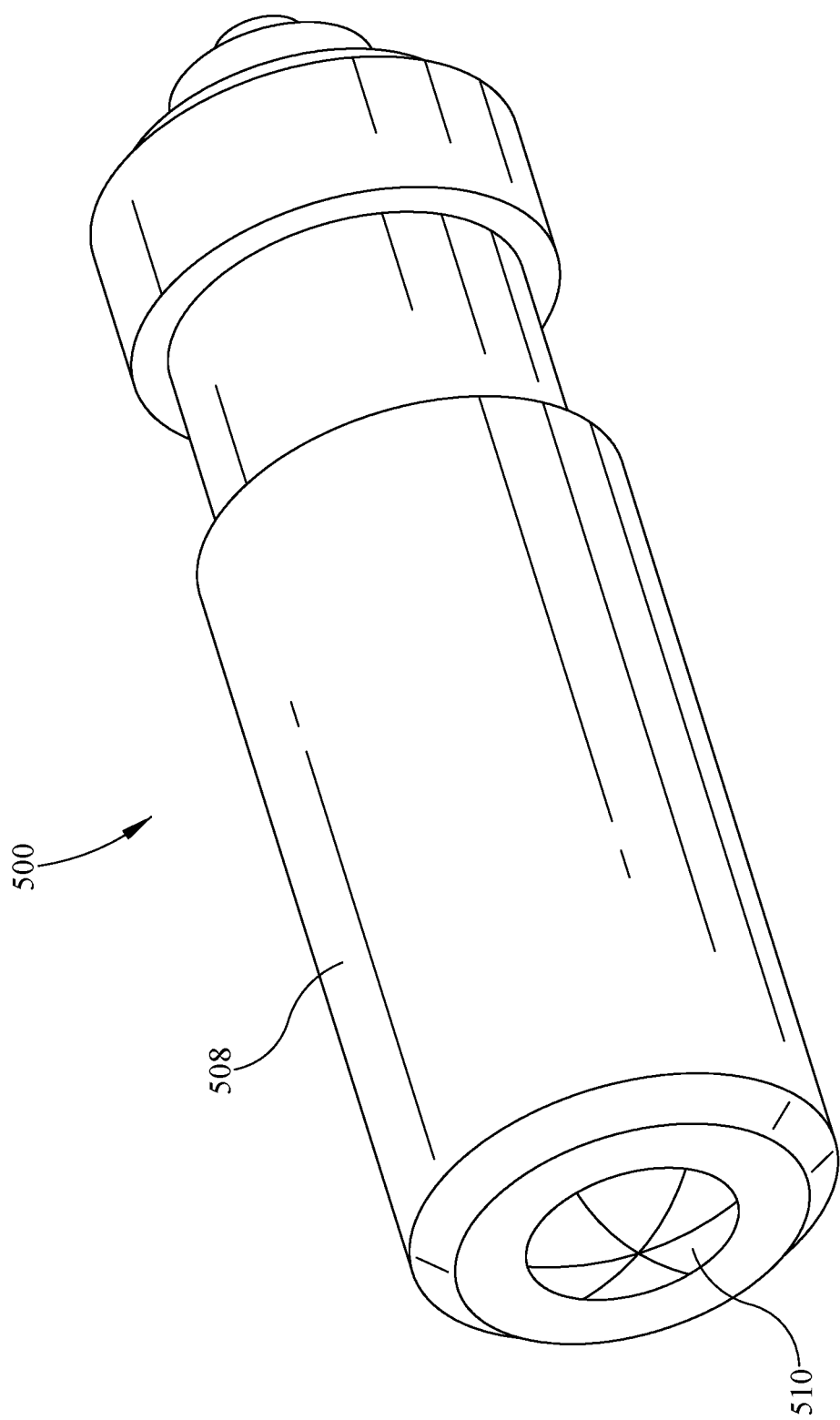
FIG. 5 is a perspective view of another self-cleaning needleless consistent with some embodiments of the invention.

Turning now to FIGS. 4A-B, another embodiment of a self-cleaning needless connector 400 is illustrated in storage position. Similar to the embodiment illustrated in FIGS. 1-3, the self-cleaning needleless connector 400 may include a connector body 402 with an inlet 404 and an outlet 406, where the inlet 404 and the 406 define a passageway through which fluid may flow. A sleeve or cover 408 may be positioned to envelop at least a portion of the connector body 402, including at least the inlet 404. The cover 408 may additionally include a septum 410 may open upon exertion of pressure (for example from the insertion of a syringe) to expose an inlet 404 configured to receive a male luer (for example, of a syringe). In some instances, the septum 410 may be recessed into the cover 408; while in other instances, such as illustrated in FIG. 5, the septum 510 may be disposed at the inlet end of the cover 508 of the self-cleaning needleless connector 500.

Also similar to the embodiment described with reference to FIGS. 1-3, the cover 408 may move from a first, expanded position, such as illustrated in FIGS. 4A-B, to a second, retracted position. For example, a user may actuate this lateral movement of the cover 408 in order to expose the inlet 404 of the connector body 402. In some instances, there may be one or more springs 420 that mechanically bias the cover 408 to an extended position (FIGS. 4A-B), and a user (for example a clinician) may actuate the compression of the spring by moving the cover 108 laterally towards the outlet 406 of the connector body 402 along an axis 414 running along the connector body 402 between the inlet 404 and the outlet 406.

Referring specifically to FIG. 4B, which illustrates a cross-sectional view depicting the internal components of the self-cleaning needleless connector 400 a passageway 430 may be defined between the inlet 404 and the outlet 406 through which fluid may flow. The interior of the connector body 402 and the cover 408 collectively form a reservoir 438 configured to contain a cleaning agent. As previously described, such a cleaning agent may include, but not be limited to, may be 70% isopropyl alcohol, chlorhexidine gluconate mixed with 70% isopropyl alcohol ("CHG+alcohol"), and 10% povidone-iodinechlorohexidine, or glutaraldehyde. When the self-cleaning needleless connector 400 is in a storage position the cleaning agent contained therein may be fluidly coupled with an abrasive surface 440 located within the cover 408 in fluid communication with the cleaning agent. The abrasive surface 440 may physically contact an exterior surface 412 of the inlet 404 such that the cleaning agent is also in contact with the exterior surface 412 of the inlet 404. In some instances, the abrasive surface 440 may include a plurality of bristles (as illustrated in FIG. 4B), which may be constructed of any number of materials as previously described herein. The cleaning agent may flow between the bristles of the abrasive substance 440 and contact the exterior surface 412 of the inlet 404 disinfecting the same.

The self-cleaning needleless connector 400 may also include an internal stop 422 that prevents the cover 408 from retracting too far when it moves laterally along the axis 414 running along the connector body 402 towards the outlet 406. This internal stop 422 may additionally include one or more openings 424 through which fluid (e.g. the cleaning agent) may flow. As a user-actuates the movement of the cover 408 laterally along the axis 414 running along the connector body 402 towards the outlet 406 the springs 420 compress and the cleaning agent is also forced laterally through the one or more openings 424 toward the outlet 406. An internal seal 426 contacts the internal stop 422 and seals the one or more openings 424 in order to eliminate or minimize leakage from the septum 410 when the cover 408 is in a retracted position and the inlet exposed to the external environment.

Additionally, similar to the embodiments described with reference to FIGS. 1-3, the cover 408 and/or the connector body 402 may include one or more sealants 418 that may eliminate or reduce the leakage of the cleaning agent from the self-cleaning needleless connector 400 though the area where the cover 408 and the connector body 402 interface. As discussed previously, these sealants 418 may be a sealing protrusion incorporated as a part of the connector body 402 (as illustrated in FIG. 4B) and/or the cover 408, or the sealant 418 may be one or more O-rings/gaskets, or any other sealing structure known.

Figure 6:
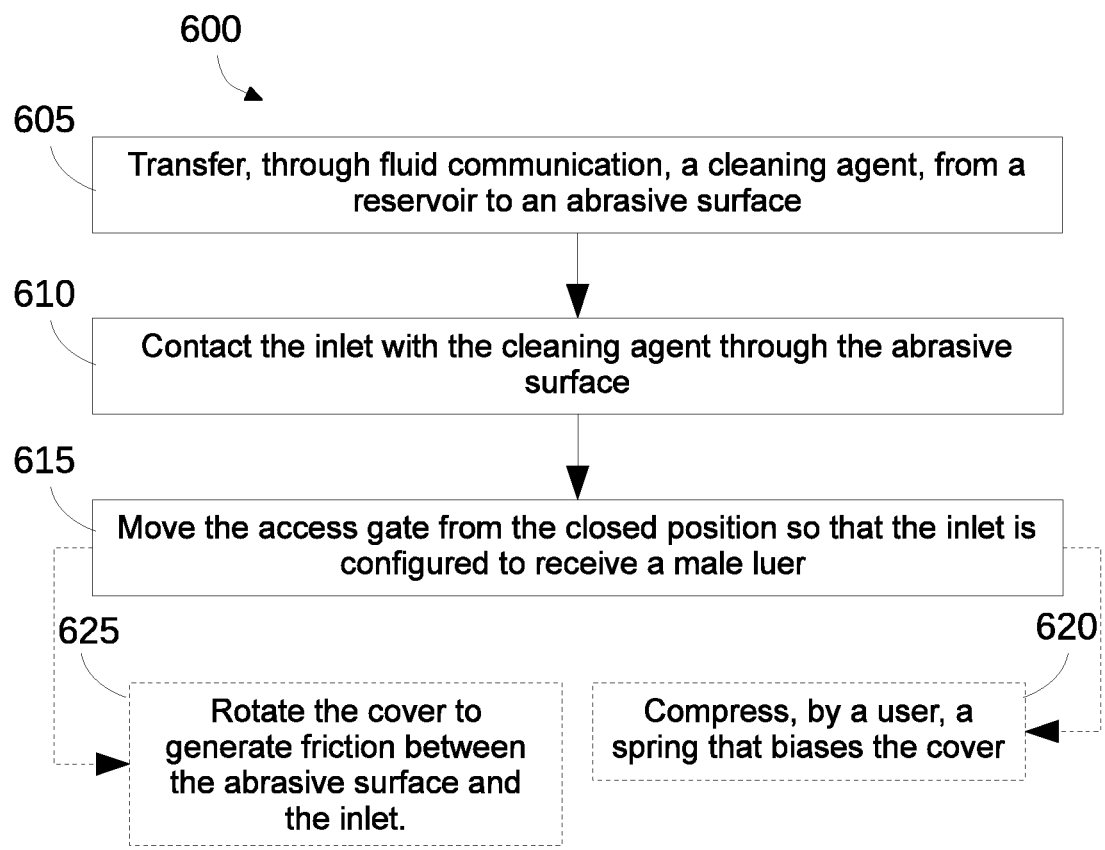
FIG. 6 is a flow chart illustrating an exemplary method of cleaning an inlet of a needless connector consistent with some embodiments of the invention.

Referring now to FIG. 6, a method 600 of cleaning a needleless connector, such as any of those described herein with reference to FIGS. 1-5. At block 605, a cleaning agent, for example 70% isopropyl alcohol, is transferred from a reservoir to an abrasive surface. The reservoir and abrasive surface may be in fluid communication, making such movement of the fluid within the needleless connector possible. At block 610, the inlet may be in contact with the cleaning agent through frictional contact with the abrasive surface.

At block 615, an access point disposed at the inlet end of the cover of the needleless connector; this access point may be moved from a first, closed position to a second, open position exposing the inlet. Once exposed, the inlet may be configured to receive a male luer. In some instances, the access point be a single piece construction that retracts into the cover when in the open position; in other instances, the access point may be a septum that moves radially between the closed and the open position.

Optionally, at block 620, the needleless connector may include a spring that mechanically biases the access point to the closed position. In such instances, the moving that occurs at block 615 may additionally include user-actuated compression of the spring.

Optionally, at block 625, the method of cleaning the needleless connector may additionally include rotating the cover about an axis of rotation generally aligned with the connector body. Such rotation may generate friction between the abrasive surface and the inlet facilitating the application of the cleaning agent to the inlet and the disinfection process. In some instances, the rotation of the cover may be simultaneous with moving the access point from the closed portion to the open position.

It will be appreciated that various modifications may be made to the embodiments discussed herein, and that a number of the concepts disclosed herein may be used in combination with one another or may be used separately. Therefore, the invention lies in the claims hereinafter appended.

What is claimed is:

1. A self-cleaning needleless connector, comprising:
a connector body defining a fluid passageway including an inlet and an outlet;
a cover disposed over at least the inlet of the connector body;
an access point disposed at an inlet end of the cover and is movable between a first position and a second position and
wherein in the first position the inlet is within the cover, and
wherein in the second position the inlet is extended beyond the cover and configured to receive a male luer;
a reservoir containing a cleaning agent;
wherein the reservoir includes an internal stop configured to prevent the cover from extending beyond the internal stop, the internal stop including one or more openings configured to allow fluid to flow through the internal stop;
an internal seal configured to abut proximate to the internal stop and the one or more openings when the access point is in the second position; and
an abrasive surface enclosed within an area generated by the cover and the access point and in fluid communication with the cleaning agent, wherein the abrasive surface and the cleaning agent are configured to contact an exterior surface of the inlet.

2. The needleless connector of claim 1, wherein the cover is movable between an extended position and a retracted position.

3. The needleless connector of claim 2, wherein a spring mechanically biases the cover to the extended position and the access point is movable to the second position upon user-actuated compression of the spring.

4. The needleless connector of claim 2, wherein a piston moves laterally towards an outlet end of the connector as the cover moves from the extended position to the retracted position to accommodate the cleaning agent.

5. The needleless connector of claim 1, wherein the cleaning agent is 70% isopropyl alcohol.

6. The needleless connector of claim 1, wherein the abrasive surface is a plurality of bristles.

7. The needless connector of claim 1, wherein the cover is rotatable about an axis of rotation that is generally aligned with the connector body.

8. The needleless connector of claim 7, wherein the cover is rotated about the axis of rotation simultaneous with the cover being moved to a retracted position by user-actuated compression of a spring, wherein the spring mechanically biases the cover to an extended position.

9. The needleless connector of claim 1, wherein the access point is configured to retract into the cover when the access point moves from the first position to the second position.

10. The needleless connector of claim 1, wherein the cover further includes one or more sealants to minimize leakage of the cleaning agent.

11. The needless connector of claim 2, wherein the exterior surface of the inlet includes a plurality of threads and the abrasive surface is configured to contact the plurality of threads as the cover moves from the extended position to the retracted position.

12. A self-cleaning needleless connector, comprising:
a connector body defining a fluid passageway including an inlet and an outlet, wherein the inlet includes a plurality of threads and is configured to receive a male luer;
a cover disposed over at least the inlet of the connector body, wherein the cover is movable between an extended position and a retracted position,
wherein in the extended position the inlet is within the cover, and
wherein in the retracted position the inlet is extended beyond the cover;
a septum disposed proximate an inlet end of the cover;
a reservoir containing a cleaning agent, wherein the reservoir fluidly connects the connector body and the cover;
wherein the reservoir includes an internal stop configured to prevent the cover from extending beyond the internal stop, the internal stop including one or more openings configured to allow fluid to flow through the internal stop;
an internal seal configured to abut proximate to the internal stop and the one or more openings when the cover is in the retracted position; and
an abrasive surface enclosed within an area generated by the cover and an access point and in fluid communication with the cleaning agent, wherein the abrasive surface and the cleaning agent are configured to contact the threads as the access point moves from a closed position to an open position.

13. The needleless connector of claim 12, wherein the cover is rotatable about an axis of rotation that is generally aligned with the connector body.

14. The needleless connector of claim 13, wherein the cover is rotated about the axis of rotation simultaneous with the cover being moved to the retracted position by user-actuated compression of a spring, wherein the spring mechanically biases the cover to the extended position.

15. The needleless connector of claim 12, wherein the septum is a split septum and is recessed into the inlet end of the cover.

16. The needleless connector of claim 12, wherein the abrasive surface is a plurality of bristles.

17. A method of cleaning an inlet of a needless connector, the method including:
providing the needless connector of claim 1;
transferring the cleaning agent, through fluid communication, from the reservoir to the abrasive surface;
contacting the inlet with the cleaning agent through the abrasive surface; and
moving the access point from the first position to the second position.

18. The method of claim 17, wherein a spring mechanically biases the access point to the first position and moving the access point from the first position to the second position further includes compressing, by a user, the spring.

19. The method of claim 17 further comprising rotating the cover about an axis of rotation that is generally aligned with the connector body, generating friction between the abrasive surface and the inlet.

20. The method of claim 19, wherein rotating the cover is simultaneous with moving the access point from the first position to the second position.

* * * * *